United States Patent
Mossbridge

(10) Patent No.: US 9,668,688 B2
(45) Date of Patent: Jun. 6, 2017

(54) METHODS AND SYSTEMS FOR CONTENT RESPONSE ANALYSIS

(71) Applicant: MOSSBRIDGE INSTITUTE, LLC, Evanston, IL (US)

(72) Inventor: Julia Mossbridge, Evanston, IL (US)

( * ) Notice: Subject to any disclaimer, the term of this patent is extended or adjusted under 35 U.S.C. 154(b) by 229 days.

(21) Appl. No.: 14/690,229

(22) Filed: Apr. 17, 2015

(65) Prior Publication Data

US 2016/0302709 A1    Oct. 20, 2016

(51) Int. Cl.
*A61B 5/16* (2006.01)
*A61B 5/00* (2006.01)
*A61B 5/024* (2006.01)

(52) U.S. Cl.
CPC ............ *A61B 5/165* (2013.01); *A61B 5/0077* (2013.01); *A61B 5/02416* (2013.01); *A61B 5/02438* (2013.01); *A61B 5/6898* (2013.01); *A61B 5/7257* (2013.01); *A61B 5/7278* (2013.01)

(58) Field of Classification Search
None
See application file for complete search history.

(56) References Cited

U.S. PATENT DOCUMENTS

| | | | |
|---|---|---|---|
| 5,676,138 A | 10/1997 | Zawilinski | |
| 6,021,346 A | 2/2000 | Ryu et al. | |
| 6,067,468 A | 5/2000 | Korenman et al. | |
| 6,520,905 B1 | 2/2003 | Surve et al. | |
| 6,585,521 B1 | 7/2003 | Obrador | |
| 7,547,279 B2 | 6/2009 | Kim et al. | |
| 8,126,220 B2 | 2/2012 | Greig | |
| 8,438,590 B2 | 5/2013 | Crenshaw | |
| 8,462,996 B2 | 6/2013 | Moon et al. | |
| 8,464,288 B2 | 6/2013 | Pradeep et al. | |
| 2008/0235284 A1 | 9/2008 | Aarts et al. | |
| 2010/0174586 A1 | 7/2010 | Berg, Jr. et al. | |
| 2013/0096439 A1 | 4/2013 | Lee et al. | |
| 2013/0345568 A1 | 12/2013 | Mestha et al. | |
| 2014/0024961 A1 | 1/2014 | Lin et al. | |
| 2014/0219566 A1 | 8/2014 | Rodriguez et al. | |

(Continued)

OTHER PUBLICATIONS

Sebastian Anthony, Real-time emotion detection with Google Glass: An awesome, creepy taste of the future of wearable computers, web article, Sep. 4, 2014, Extreme Tech, avaiable at http://www.extremetech.com/extreme/189259-real-time-emotion-detection-with-google-glass-an-awesome-creepy-taste-of-the-future-of-wearable-computers (last accessed Jun. 23, 2015).

(Continued)

*Primary Examiner* — Eileen Adams
(74) *Attorney, Agent, or Firm* — Cherskov Flaynik & Gurda, LLC

(57) ABSTRACT

A data processing device controls the image-recording device to capture a video, turn the video into a time series of luminance values, and analyzes the frequency spectrum of this time series. The device determines whether said series of images depicts a test subject. The device extrapolates the emotional response of a detected test subject to choices displayed on the display device during a time period encompassed by said series of images. The extrapolation of the emotional response measures the subject's time between heart rate events, the associated frequency spectrum, and where said captured video comprises a close-up depiction of a region of the subject's exposed skin.

8 Claims, 13 Drawing Sheets

(56) References Cited

U.S. PATENT DOCUMENTS

2015/0148687 A1* 5/2015 Kitajima ............ A61B 5/02427
600/477
2016/0089031 A1* 3/2016 Hu ....................... A61B 5/6892
600/480
2016/0127641 A1* 5/2016 Gove .................... G06T 1/0007
348/143

OTHER PUBLICATIONS

Kieron Monks, Feeling glum, happy, aroused? New technology can detect your mood, web article, Feb. 6, 2014, CNN, available at http://www.cnn.com/2014/02/04/tech/innovation/this-new-tech-can-detect-your-mood/ (last accessed Jun. 23, 2015).

Daniela Palomba et al., Visual evoked potentials, heart rate responses and memory to emotional pictorial stimuli, International Journal of Psychophysiology, Jul. 1997, pp. 55-67, vol. 27, Issue 1, Elsevier, Amsterdam, Netherlands.

Scott R. Vrana et al., The startle probe response: A new measure of emotion?, Journal of Abnormal Psycholorgy, Nov. 1988, pp. 487-491, vol. 97, Issue 4, American Psychological Association, Washington DC, USA.

* cited by examiner

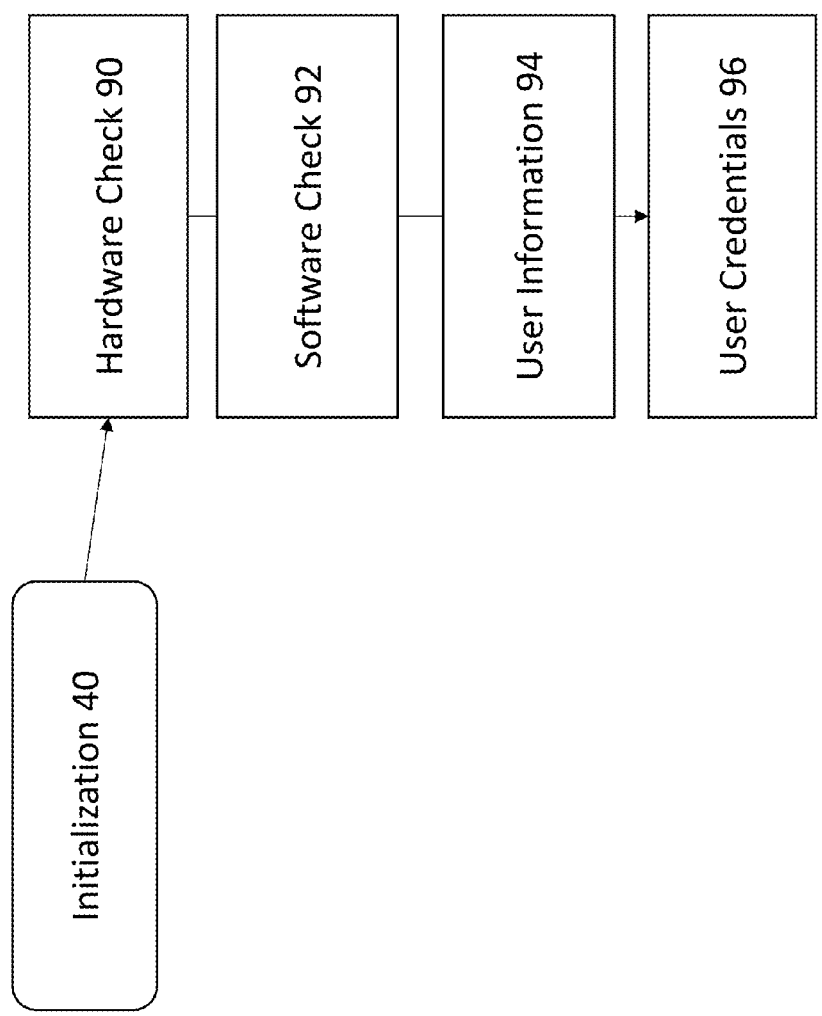

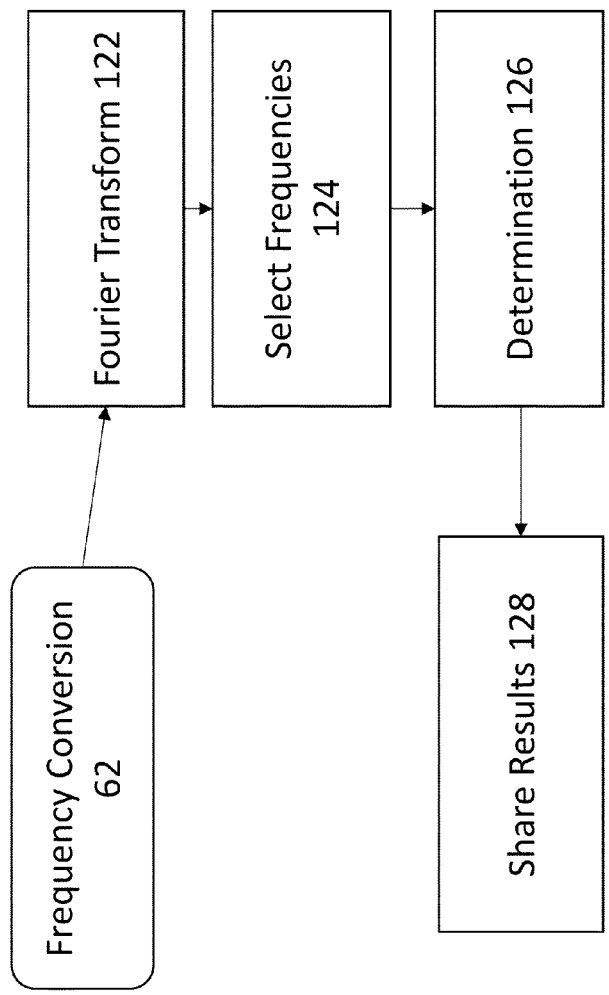

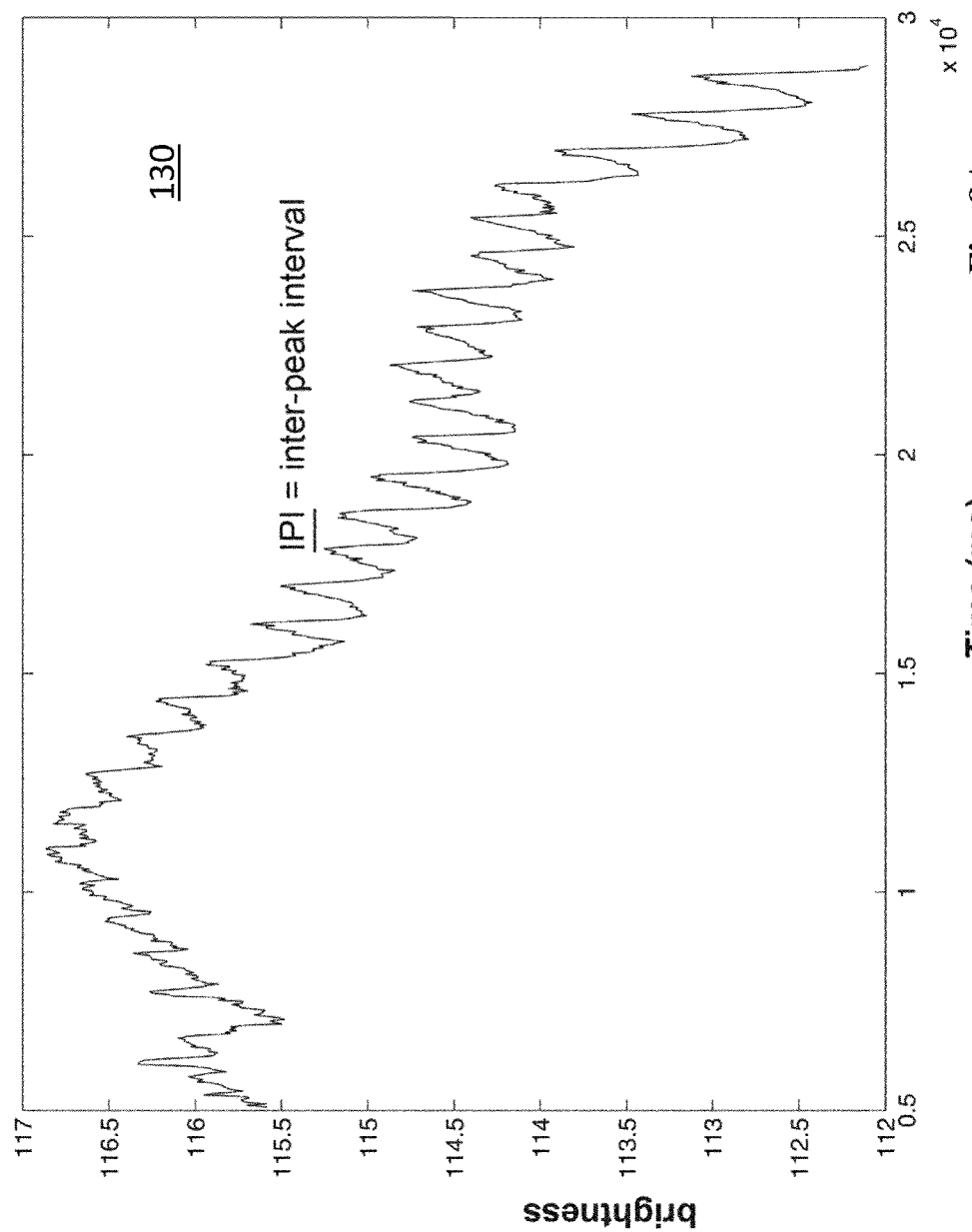

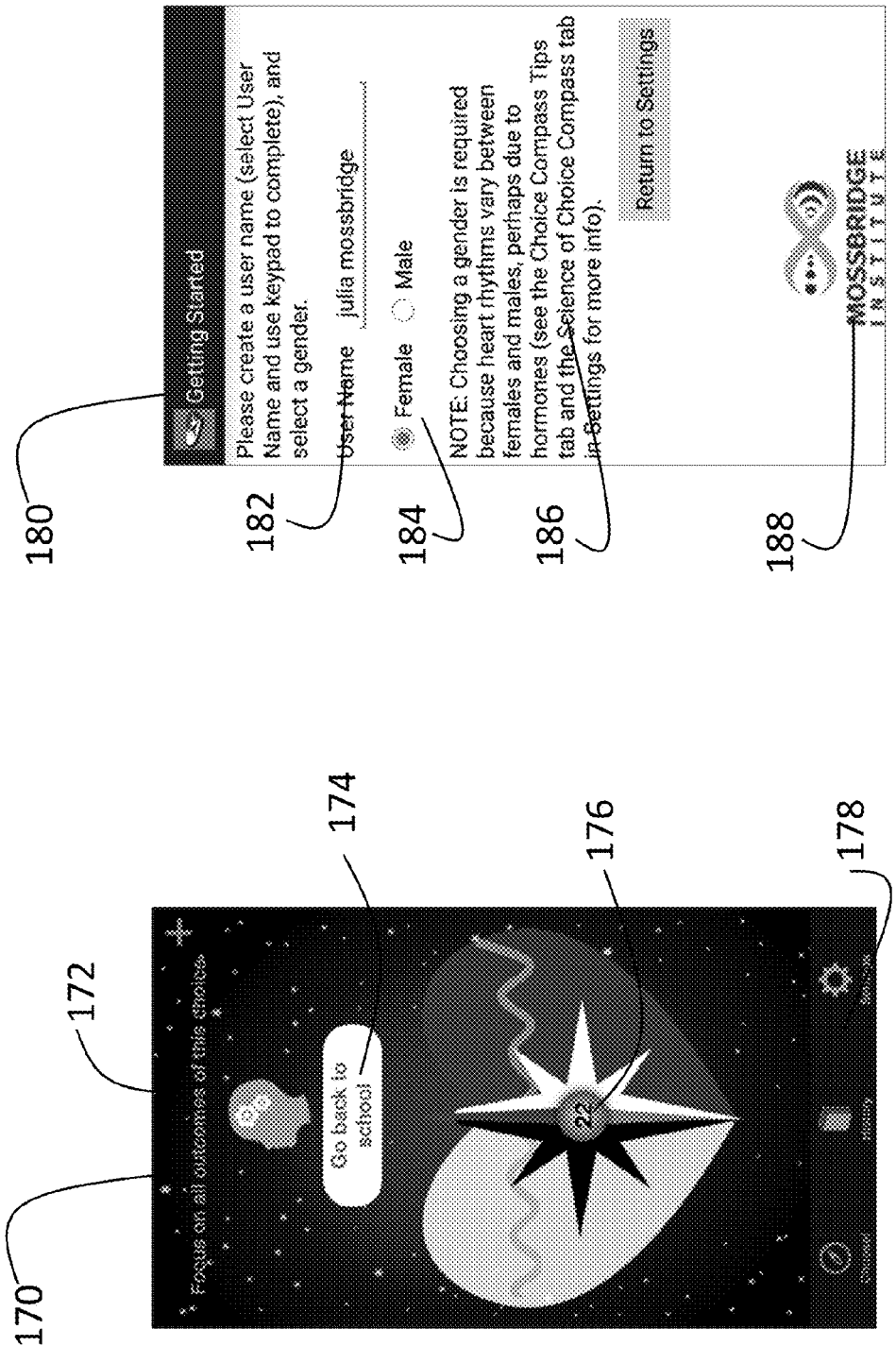

METHODS AND SYSTEMS FOR CONTENT RESPONSE ANALYSIS

BACKGROUND OF THE INVENTION

1. Field of the Invention

In one embodiment, the method and system conveys information about a psychophysiological response to one or more choices presented to a user. The system employs a standard camera, such as a multi-purpose camera in a portable device.

2. Background of the Invention

Methods and devices for measuring responses to external stimuli are known in the art. Various earlier attempts include coupling a user to a direct biological measurement device, such as a wrist strap to measure heart rate while the user is exposed to particular stimuli. Other systems employ facial recognition to determine a response to a particular event, such as a video being shown concurrently as the facial responses are being recognized.

A need exists in the art for a non-cumbersome system to measure responses to choices and assist an end user in making choices.

SUMMARY OF INVENTION

An object of the invention is to provide a means to evaluate psychophysiological responses to choices by an end user.

Another object of the invention is to provide a user with several choices, with two alternatives being presented in one embodiment. A feature of the invention is that psychophysiological responses to each choice are compared. An advantage of the invention is that the system can provide information about which alternative has a more positive profile for the end user or certain other authorized third parties.

A further object of the invention is to provide a user with feedback on choices. A feature of the invention is that psychophysiological responses to each choice are compared. An advantage of the invention is that the system can provide information about which alternative is linked to a more positive mood state for the user.

Another object of the invention is to enhance user decision-making by providing a system that does not require sensors beyond those already existing on portable devices. A feature of the invention is that psychophysiological responses to each choice are analyzed using a smartphone, in one embodiment. An advantage of the invention is that the system can provide end user with feedback without relying on expensive sensors.

Another object of the invention is to provide an unobtrusive way to measure emotional responses. A feature of the invention is that emotional responses to choices can be measured in short amounts of time. An advantage of the invention is that an emotional response can be measured without an interruption to the user's schedule.

Another object of the invention is to provide the user with supportive information by professionals. A feature of the invention is that emotional responses may be transmitted to third parties providing support to the end user. An advantage of the system is that the treating professionals have insight into the end user's psychophysiological preferences.

A further object of the invention is to provide users with several types of analysis in one device. A feature of the invention is that the system calculates both mean time between heart rate peaks as well as frequency representations of the data. A benefit of the system is that it can calculate multiple types of outputs for analysis using one set of inputs.

An additional object of the invention is to provide users with private analysis. A feature of one embodiment of this invention is that no data points are shared with outside entities and all calculations occur within the user device. An advantage of the invention is that the user can make individual queries about his or her psychophysiological state without third party interventions.

A data processing device controls the image-recording device to capture a video: determine whether said series of images depicts a test subject and extrapolate the emotional response of a detected test subject to choices displayed on the display device during a time period encompassed by said series of images wherein the extrapolation of the emotional response measures the subject's time between heart rate peaks and wherein said captured video comprises a close-up depiction of a region of the subject's exposed skin, and wherein the time between heart rate peaks is converted to the frequency domain.

BRIEF DESCRIPTION OF DRAWING

The invention together with the above and other objects and advantages will be best understood from the following detailed description of the preferred embodiment of the invention shown in the accompanying drawings, wherein:

FIG. 3 depicts a schematic view of the initialization steps of one embodiment of the system;

FIG. 7 depicts a schematic view of additional analysis steps of one embodiment of the system;

FIGS. 8A-C depict time, inter-peak interval, and frequency data used by one embodiment of the system; and FIGS. 9A-F depict sample screens of one embodiment of the system.

DETAILED DESCRIPTION OF THE INVENTION

Figure 1:
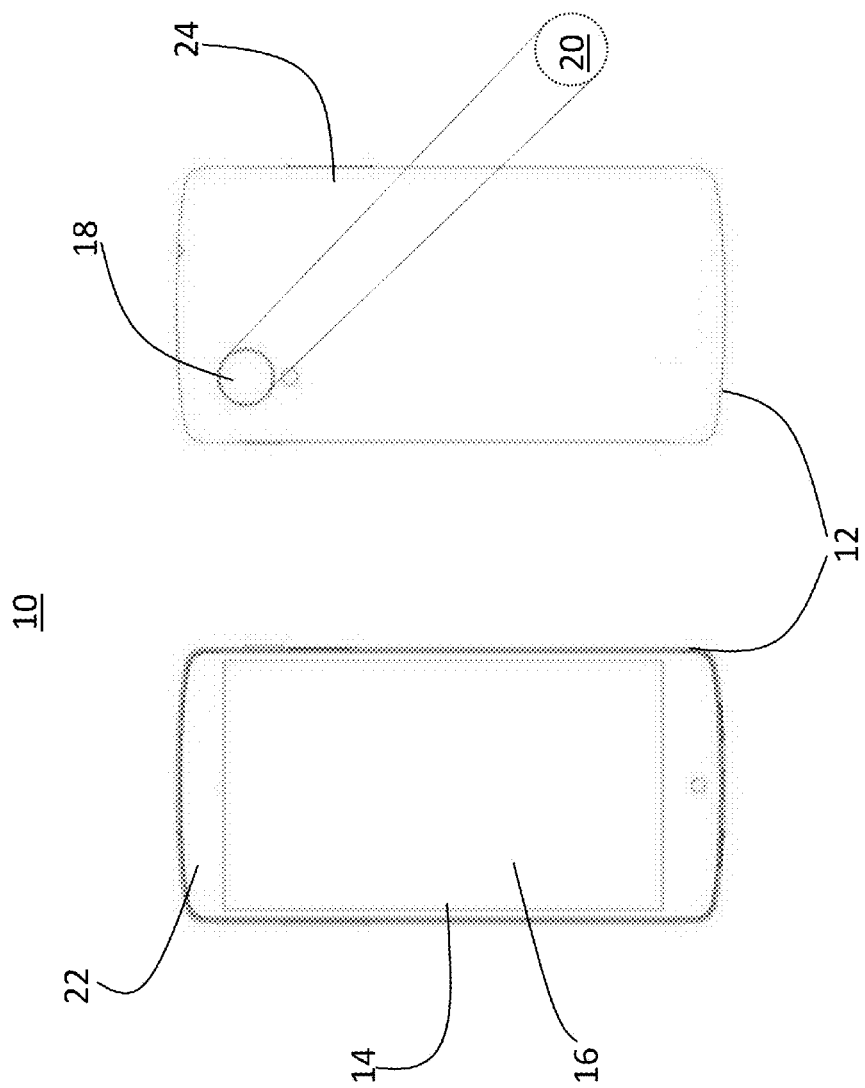
FIG. 1 depicts an overview of one implementation of the system.

The foregoing summary, as well as the following detailed description of certain embodiments of the present invention, will be better understood when read in conjunction with the appended drawings.

To the extent that the figures illustrate diagrams of the functional blocks of various embodiments, the functional blocks are not necessarily indicative of the division between hardware circuitry. Thus, for example, one or more of the functional blocks (e.g. processors or memories) may be implemented in a single piece of hardware (e.g. a general purpose signal processor or a block of random access memory, hard disk or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Beginning with FIG. 1, in one embodiment, the system 10 comprises a multi-purpose device 12 having a display 14 and one or more input means. In one embodiment, the input means comprises a touchscreen interface 16 on the multi-purpose device 12. In other embodiments, the input means comprises user interface elements such as push buttons, scroll wheels, and other appropriate selection devices.

The multi-purpose device 12 also includes at least one imaging device, such as a camera 18. In a different embodiment, the multi-purpose device uses a variety of sensors in place of the camera 18. The camera 18 includes one or more sensors and outputs images containing luminosity data for a captured image. One implementation of the system is on a portable general-purpose computer, such as a phone, tablet, or laptop. In another embodiment, the system is implemented on dedicated hardware comprising a processor, memory, storage, camera, display, and user interface. In one embodiment, the only sensor used by the system is the camera 18, to the exclusion of EEG sensors, and other special-purpose heart rate detectors. The system excludes a direct measurement of heart rate, respiration, perspiration rate, facial recognition, and other tasks commonly associated with detecting emotional responses.

The camera 18 captures images. For each captured image, the camera provides luminosity values 20 for color components, including red, green, blue, and brightness. The brightness information is used for scale purposes—in one embodiment. In this embodiment, if large amounts of light are allowed into the aperture (thereby increasing brightness), then the scale is adjusted to compensate for the light amount.

As shown in FIG. 1, in one embodiment the multipurpose device 12 is a phone with a user-facing side 22 and a reverse side 24.

Figure 2:
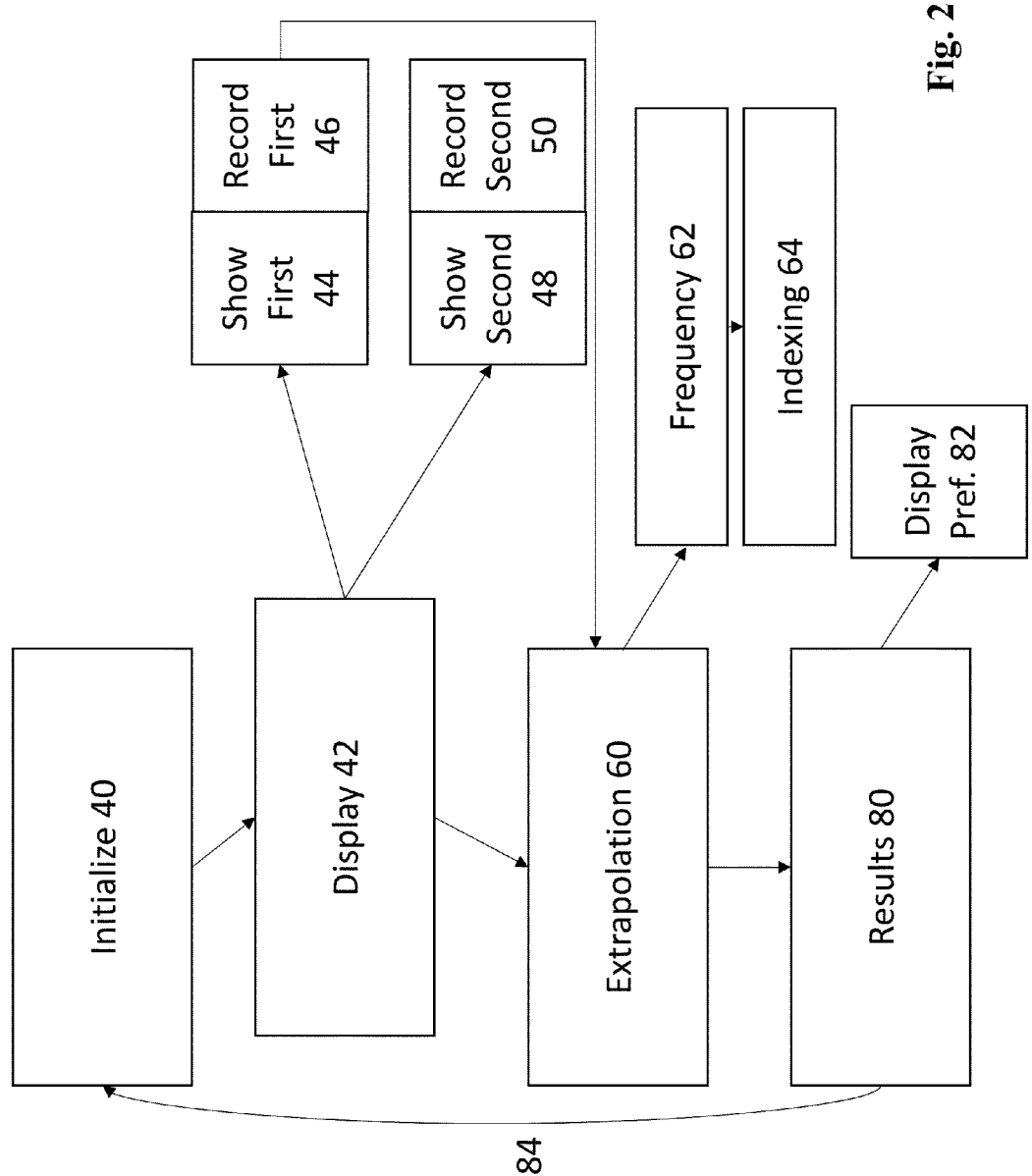
FIG. 2 depicts a schematic overview of one implementation of the system.

In use, as shown in the broad overview flow chart of FIG. 2, the system 10 is initialized 40 to provide instructions to the user.

The instructions to the user include asking the user to align the device 12 camera 18 such that the camera 18 is pointed to the user's exposed skin.

Once the user has acknowledged that the preparatory steps are completed, the system 10 proceeds to the presentation step 42. In one embodiment, in this step, the user is shown a first presentation 44 and asked to focus on that presentation 44. In a further embodiment, the first presentation 44 is one of two possible binary choices. For example, the choice may evoke a particular emotional response. The source of the first presentation 44 may be an authorized third party such as a researcher, a therapist, or analyst. In another embodiment, the user selects their own binary choice during the first presentation 44 the first of the binary choices is shown. In another embodiment, the first presentation 44 may not be a choice, but instead consist of sounds or images, such as words, music, and/or nature sounds. Regardless of the embodiment, this user experience will be referred to as the "first presentation."

In one embodiment, while the user is focused on the first presentation (or otherwise interacting with the first presentation), the camera 18 is engaged and captures a first series of images 46 of the user's exposed skin.

In one embodiment, each image of the first series of images 46 comprises the luminosity values 20 of all colors of the user's exposed skin, with another embodiment, only certain values 20 are recorded.

As an indicator of the first presentation 44 remains on the display 14 for a period of time indicated to the user during the initialization step 40. In one embodiment, the length of time is controlled by the user, in other embodiments, the length of time is determined by the presentation 44 being shown to the user. In another embodiment, the user is asked to indicate to the system when the time to view the first presentation should cease, such as by pressing a user interface element within the device 12 or issuing a verbal command to the device 12. Finally, in other embodiments, the multi-purpose device comprises a user-facing camera and the user is shown the presentation so long as the users' eyes are focused on the presentation such as an image or video clip.

The system thereafter proceeds to show the user an indicator of the second presentation 48. In one embodiment this indicator is a request that the user perform the second task (such as concentrating on a second of two binary choices). In another embodiment, this indicator urges the user to observe/listen to a stimulus. As was the case with the first presentation 44, during the second presentation 48, the device 12 camera 18 takes a second series 50 of images comprising a video of the user's skin.

In one embodiment, the time period during which the first presentation 44 and second presentation 48 are shown is fifty seconds. In one embodiment, if the time period is lower than fifty seconds, insufficient data would be gathered from the input.

The system then proceeds to the extrapolation step 60. During this step, the first series of images 46 is compared with the second series of images 50, to determine which image had a more favorable emotional response from the user.

In one embodiment, the analysis proceeds by extracting the luminosity values 20 of each image from each series 46, 50. The analysis proceeds to convert the luminosity values for each image in the series 46, 50 into heart rate peak values, resulting in calculated interpeak intervals.

Having calculated the inter-peak intervals, the system performs a Fast Fourier Transform (FFT) on the time series of inter-peak intervals to generate the frequency information 62.

In one embodiment, the fast-Fourier transform occurs on the multi-purpose device 12, while in another embodiment the fast-Fourier transform occurs at a different location.

The system then compares the power spectrum created by the FFT from inter-peak interval data from the first presentation with that from the second presentation. During a testing phase, the FFTs of these two presentations are stored and analyzed to determine, across multiple users who had the same first and second presentations, which frequency bins contain information that separates the first from the second presentation, based on mood, preference, or other factor (which will depend on the content of the first and second presentations and the purpose of the differentiation). During a final, end-use phase, the FFTs of these two presentations are stored and frequency bins that were found to be useful in differentiating the two presentations during the testing phase are compared and a results set related to the differences in these frequency bins is created.

Once the Extrapolation step 60 is concluded, in a final end-user phase, the system presents the end user an index related to the results set 80. In one embodiment, the results set 80 is an indication 82 of which of the two presentations are preferred by the user. In other embodiments, the system includes feedback for the end user about which of two choices produced a more positive response when the user was thinking about each respective option.

In other embodiments, the system proposes to the user to restart the process 84 with new presentations on the basis of the preferred 82 at the current iteration.

The details of each step described herein will be addressed below.

Initialization Steps

FIG. 3 shows the steps of the initialization of the system. The initialization step 40 comprises several verification steps. In one embodiment, with the system 10 running on a multipurpose device 12, the system first undergoes a hardware check 90. The hardware check 90 ensures that the device has sufficient storage and processing capability and that any required computational libraries are available. In one embodiment, the hardware check 90 also verifies the functioning of at least one camera, invoking the test operations integrated into the multipurpose device 12. In another embodiment, where the system does not use a camera but instead a different sensor, the hardware check 90 confirms that the sensor is providing viable information.

In an embodiment where the system 10 operates on a stand-alone device, such as a smartphone, the initialization step 40 also checks the integrity of the software 92. In one embodiment, the software file size and a checksum value is verified for the main software executable 92. This ensures that the software has not been tampered and that the hardware is not malfunctioning.

Following a successful verification of hardware, the system proceeds to displaying one or more screens of user information 94, in one embodiment. In this embodiment, the user information includes information about the purpose of the software as well as providing the user an opportunity to practice the steps required by subsequent analysis. In one embodiment, the user is asked to place their figure near the camera aperture to take a preliminary reading.

The user is also provided information about the applicable privacy policies and the use of the information by third parties. In one embodiment, no data is shared with external parties. In another embodiment, only heartrate data and technical data from the session are available to external parties. In another embodiment, the user information 94 provides the user an opportunity to share the information with third parties, such as a therapist or another third party.

While in FIG. 3, the hardware check 90 and user information check 94 are shown as separate consecutive steps, in some embodiments, the steps occur concurrently. In one such embodiment, the hardware check 90 and software check 92 occur while the user information step 94 is waiting for user feedback or acknowledgement.

Following the review of the user information 94, the user is asked for credentials 96. In one embodiment, the user credentials 96 include identifying information. In another embodiment, the user credentials 96 allow for anonymous use of the application. However, the user credentials 96, in some embodiments require the user to provide demographic information such as the user's biological gender, last menstrual period where applicable, and age group. In another embodiment, only the user's username and gender is required as the user credentials 96.

Figure 4B:
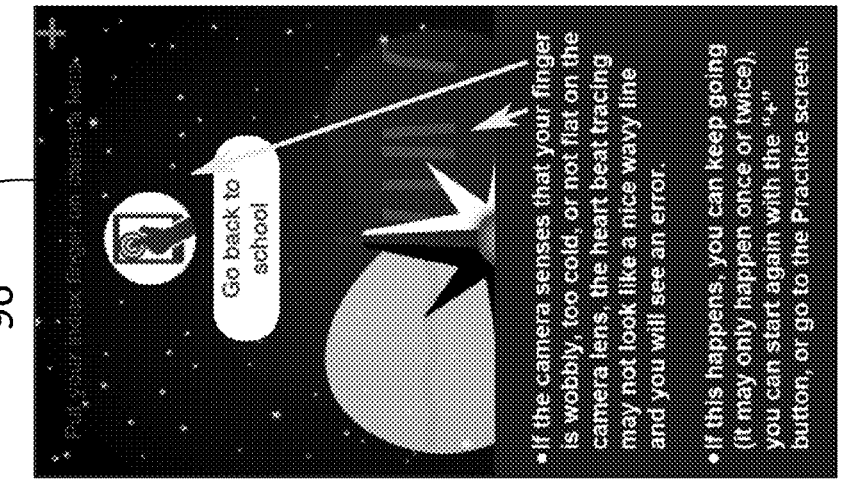
FIGS. 4A-B depict sample screens used by one embodiment of the system.
Figure 4A:
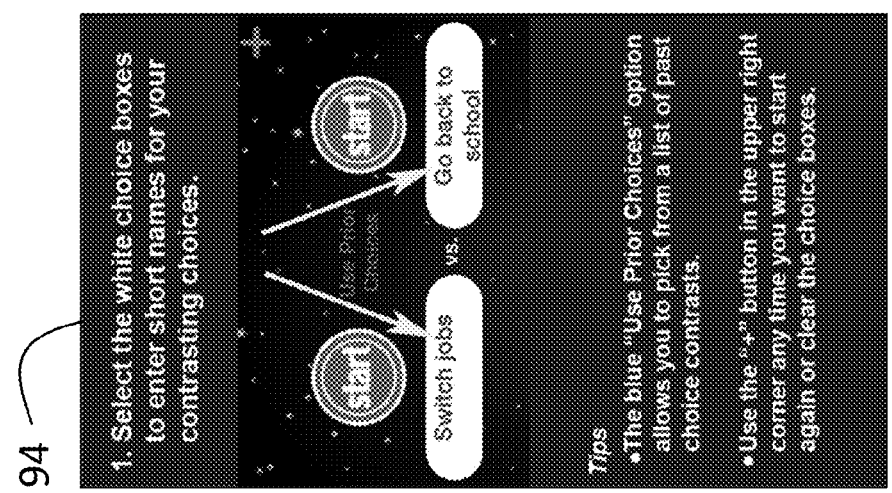

Pursuant to one embodiment, a screen showing user instructions 94 is shown in FIG. 4A and a screen showing additional instructions 96 is shown in FIG. 4B.

Display and Reading

Figure 5:
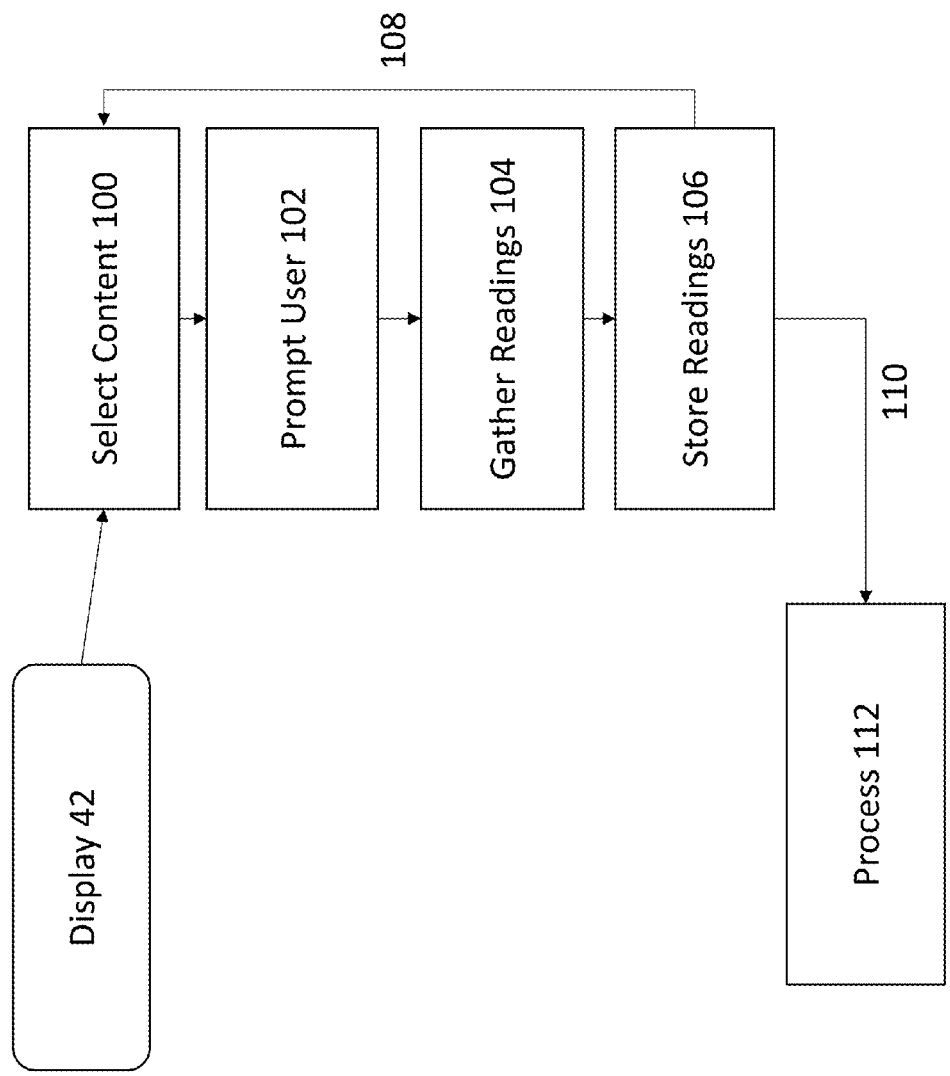
FIG. 5 depicts a schematic view of the user interaction steps of one embodiment of the system.
Figure 6:
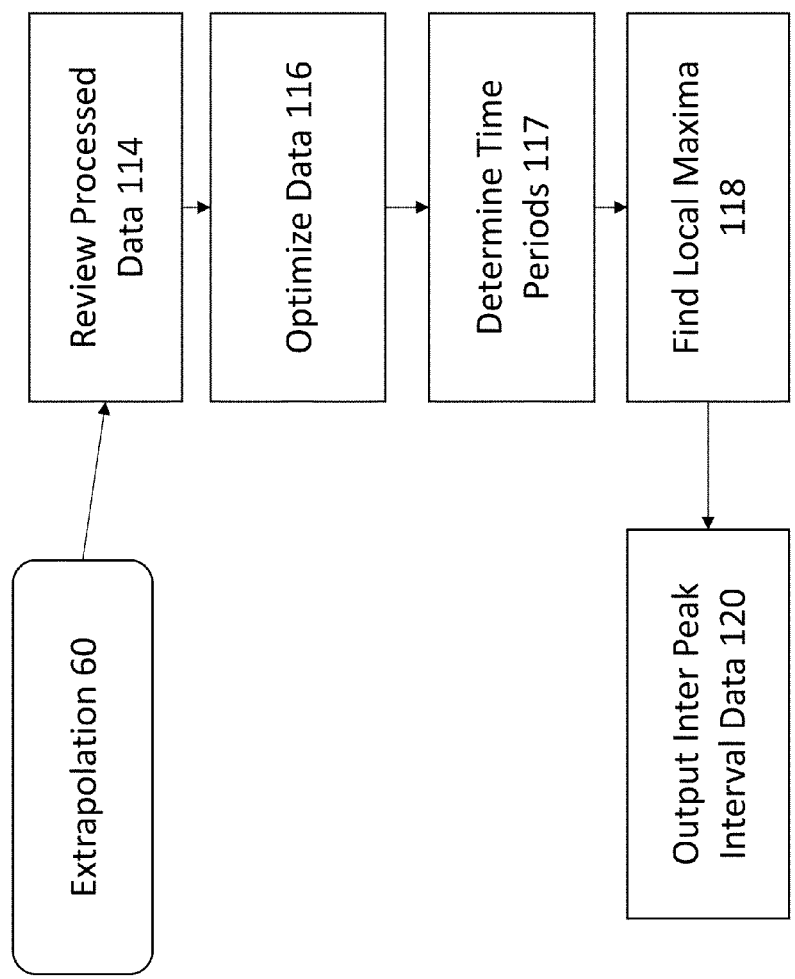
FIG. 6 depicts a schematic view of the analysis steps of one embodiment of the system.

Turning now to FIG. 5, depicted there is a schematic of the display step 42, which occurs after the initialization step 40.

Following receiving instructions as part of the user information steps 94, the user is asked to select content 100. In one embodiment, the first display step 42 includes one type of content, while the subsequent display step 48 would use different content. In this embodiment, the select content step 100 applies to only the first display step 42. In another embodiment, the select content step 100 selects content for both display steps 42.

The select content step 100 is not limited to pictorial content. In one embodiment, the select content step 100 allows the user to choose from a plurality of content, including video, three-dimensional models, or audio files. In another embodiment, the select content step 100 asks the user to read a text selection and focus on the text. In another embodiment, the select content step 100 involves requesting that the user select content that the user will be prompted to imagine or think about rather than showing content directly to the user.

In one embodiment the content selection step 100 uses the local device as the source of the content to be shown to the user. In another embodiment, the content to be shown to the user is instead selected from an external server or a multitude of servers.

In one embodiment, the content selection step 100 asks the user to select content without significant limitations. In another embodiment, the user-selection options during the content selection step 100 are limited by the type of decision the user is seeking to make. For example, if the user is determining what course of action will make the user psycho-physiologically happier, the content selection step 100 will allow user to make selections that are relevant to the alternative courses of action.

In another embodiment, the content selection step 100 provides the user with only limited options as the content is selected by an authorized third party, such as a therapist or other professional. In one embodiment, the select content step 100 does not provide the user with any option, but rather prompts the user that the process will begin shortly.

Following the content selection step 100, the user is prompted with the content during the prompting step 102. During this step, the user is asked to consider the content, while exposing the users' skin to the sensor, such as the camera 18. The prompting step 102 occurs for a duration that is sufficient to collect reliable readings, in one embodiment that duration is at least fifty seconds.

During the prompting step 102, the user is asked to focus on the selected content 100, whether that content is actually displayed to the user, or simply the user is asked to consider the content in their mind.

Further, during the prompting step 102, the system ensures that the user is complying with instructions displayed during the user information step 94. If the user is no longer providing sensor readings, such as would occur if the user removes a finger from the camera aperture, the prompting step 102 includes one or more reminders for the user. Further, the prompting step 102 includes a timer of the duration of the readings provided by the user. In one embodiment the timer is shown to the user, in another embodiment, the timer is not shown to the user.

During the user-prompting step 102, the system also gathers readings 104 from the user. In one embodiment, the readings comprise a video of the user's skin. In another embodiment, the readings comprise direct sensor readings, for example, from a direct contact skin sensor.

The gathered readings 104 are stored 106 for additional processing by the system. In one embodiment, the storing of readings 106 is performed using a non-volatile storage medium integrated to the device taking the readings, in another embodiment an external storage device is used.

While in the flowchart of FIG. 5, the steps are shown as distinct entries, in one embodiment several steps occur concurrently. For example, the gathering of readings 104 occurs while the user is interacting with the content during the prompting step 102. In one embodiment, the readings 104 comprise a large quantity of data, such as a large video file and so the information is written to storage not only at a single store readings step 106, but throughout the process.

Upon the storage of the first set of readings 106, the process iterates 108 a second time by returning to the select content step 100.

In one embodiment, the content selected at the second iteration of the content selection step 100 is a different choice from the first selected content 100. In this way, the readings gathered at the second iteration of the gather readings step 104, will be distinct from the readings at the first iteration.

Upon completed storage of the second iteration of readings 106, the system exits the iteration 110 and moves to the processing steps 112. In this embodiment, the processing steps occur only after both iterations are completed. In another embodiment, processing occurs after each iteration. With this embodiment, if the results of the gathered readings 104 are inconclusive or somehow not useable, the system can iterate again should additional iterations be possible.

In yet another embodiment, the iteration 108 occurs more than twice, with a third or subsequent iteration of the content selection step 100, the prompt user step 102, the gather readings step 104, and the store readings step 106 occurring. In this embodiment, the user is provided with multiple alternatives to consider during the content selection step 100. In another embodiment, the user receives multiple presentations, one for each content selection step 100.

Peak Extrapolation Step

Upon receiving data from storage in the process data step 112, the system moves to the extrapolation phase 60. During this phase, the system first reviews the processed data 114 to determine the type of sensor used.

In the embodiment that uses a video camera 18 to record an area of the user's skin, the data will comprise video frames with each frame having red, green, blue, and brightness information for each pixel. In one embodiment, the color data is first optimized 116 to remove several channels, specifically focusing only on red and green values. Therefore, the processing step 116 decreases the amount of further calculations by 50% by eliminating two of the four data values for each pixel, in this embodiment. Nonetheless, the information conveyed by the two relevant channels remains significant to the final results sought.

In an embodiment where the data 114 indicates that a skin sensor of heart rate information was used, the optimization step will review the data to see if there are any anomalies, as would happen if the sensor lost connection to the user briefly. Further, if the sensor has a higher resolution than needed, the optimize data step 116 would smooth out the data from the sensor, removing unnecessary data points (downsampling), further decreasing the amount of calculation necessary.

In an embodiment using a camera, the data comprises 17-40 frames per second lasting from 50 to 75 seconds. Each frame is represented by the average of the two values per pixel, with the values averaged across all pixels in the frame. The time of obtaining each frame is stored along with each frame.

In a different embodiment, the optimization step 116 further decreases the number of data points that the system must calculate by averaging the values for each frame that do not exceed threshold values. The resulting optimized data comprises only relevant two values (a first for the red value, a second for the green value) for each frame that represent skin-tone values, further decreasing the computational load on the system.

The result of the local-maxima step 118 is a recorded list of times at which local maxima occur, as according to a peak-finding algorithm. From this list, the durations of inter-peak intervals (the number of milliseconds intervening between peaks) is calculated and recorded, generating a list of the inter-peak interval data 120.

In one embodiment, the inter-peak interval will vary from 500 ms to 700 ms.

The inter-peak data 120 is subsequently analyzed by the frequency conversion.

While the inter-peak data is reviewed by the system, the system is not focused on the values associated with the actual peaks. No conclusions are drawn from when the peaks occur. Rather, it is the inter-peak interval that data that are converted to the frequency domain for purposes of the analysis steps described below.

Frequency Conversion

The inter-peak interval data 120 provides some insight, but in one embodiment, the conclusions of the system are drawn from the frequency representation of the inter-peak interval data 120 instead of the data directly. In this embodiment, the frequency conversion step 62 uses as input the inter-peak interval data 120 and operates a Fast Fourier transform 122 on the data. The resulting information is represented in the frequency domain as a power spectrum.

The system thereafter examines the values at particular frequencies by selecting one or more frequencies during the selection step 124. In one embodiment, the frequencies analyzed include the frequencies between 0 and 0.048 Hz, as well as 0.244 to 10.0 Hz (assuming a sampling rate of 25 Hz and a duration of 50 seconds). The particular frequency values of interest selected for review and outcome determination depend on the output of the testing phase, which has been used to determine the frequency values that most uniquely and consistently differentiate the two types of presentations being used in an embodiment.

Following the selection 124 of one or more frequencies, a determination 126 of the user's psychophysiological state is performed. In one embodiment, this determination compares the frequency representation 124 of the first iteration of the process versus the frequency representation 124 of the second iteration of the process. The preferred presentation will have the value that most closely matches the index already obtained during an earlier controlled testing phase.

For example, in one embodiment, the values of the indices for the two presentations are summations of the respective selected frequencies 124 bins:

$$\text{sum(Values of Frequencies(0.51 Hz to 1.17 Hz))}/\text{average(Values of Frequencies(0 Hz:0.05 Hz))}$$

(assuming a sampling rate of 25 Hz and a duration of 50 seconds)

In one embodiment, the testing phase uses a combination of visual analysis and pattern classification software to select the greatest differences between the two iterations.

Thus, in the testing phase, the determination 126 thereafter quantitatively captures these differences using arithmetic, statistical, and even a second run of FFT operations on the FFT output. Once these are quantified, the determination 126 determines whether these differences are statistically significant across hundreds of people. If they are, the algorithm is then tuned to include as many of these consistent differences as possible.

Using this method, the determination 126 has detected a gender difference, in that the algorithms that focus on features of FFT data 122 from women's contrasting positive versus negative presentations flag the opposing presentation when applied to men's data. In one embodiment, the opposite direction as well is used by the determination step 126—algorithms tuned to features of FFT data from men's contrasting tasks select the opposing task when applied to women. Thus the system queries each user to choose a gender during the user credential step 96.

In one embodiment, the determination step 126 is performed before the system is available to the end-user, during a data gathering and test phase. During this test phase, the frequency bins of interest are designed and types of calculations on end user data designed.

Finally, in the final end-user phase, the conclusions of the system are shared 128 with the end user. The end user is asked to repeat the process using different inputs, or end the interaction with the system. The user may have the option to share the results with certain authorized third parties.

Figure 8B:
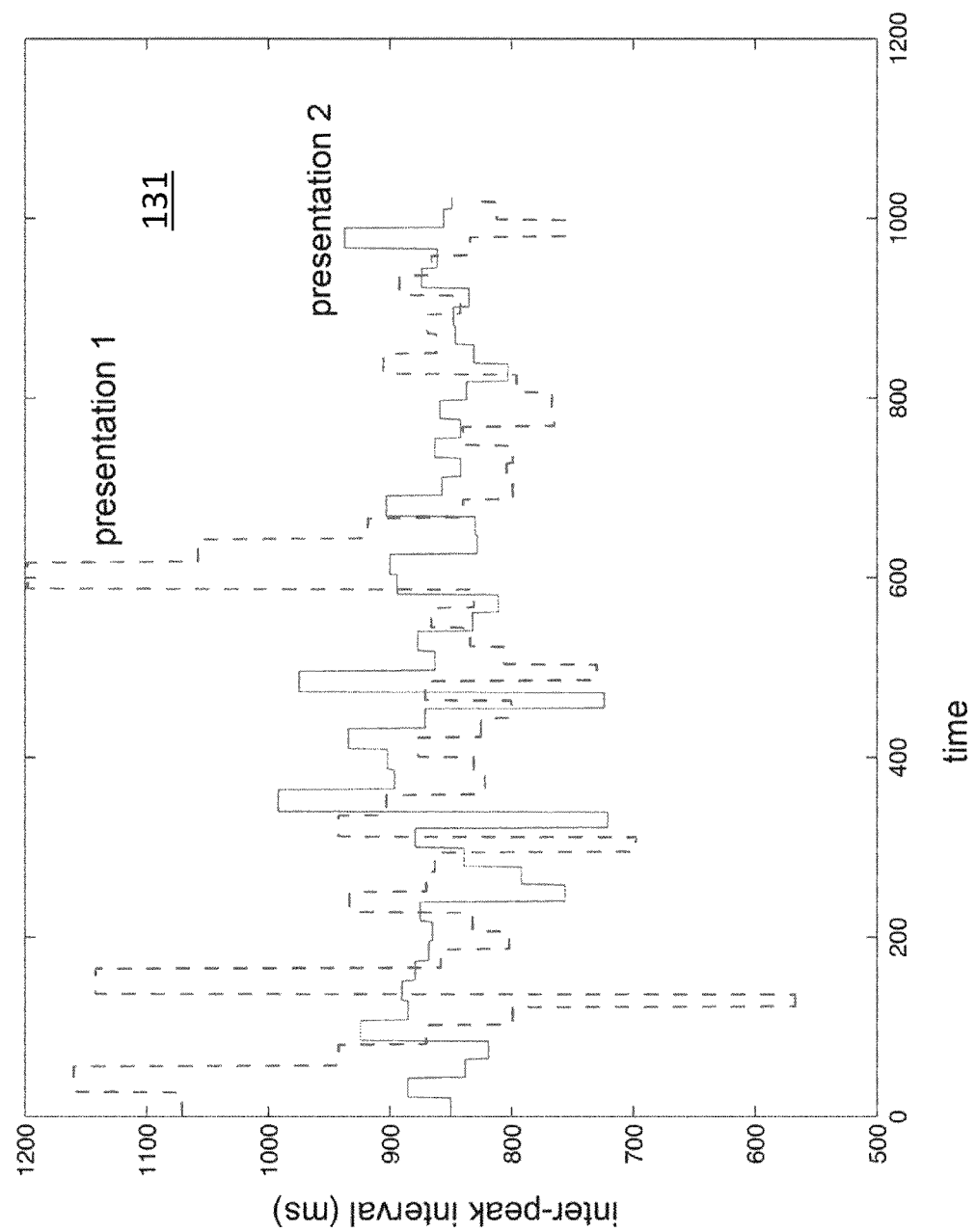
Figure 8C:
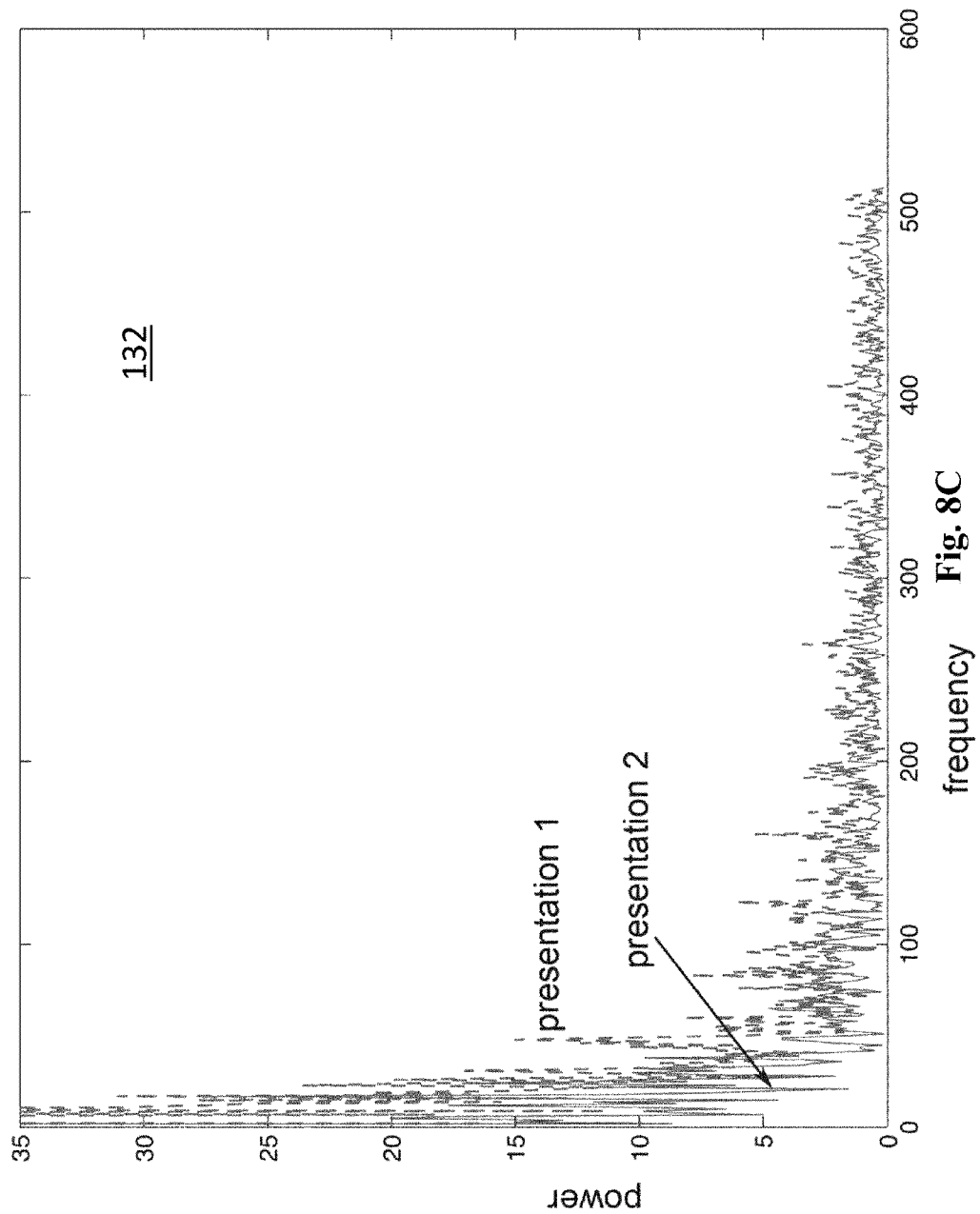

A sample chart 130 of brightness data is depicted in FIG. 8A. The corresponding interpeak data chart 131 is shown in FIG. 8B. Finally, the corresponding frequency data chart 132 is depicted as FIG. 8C.

Figure 9B:
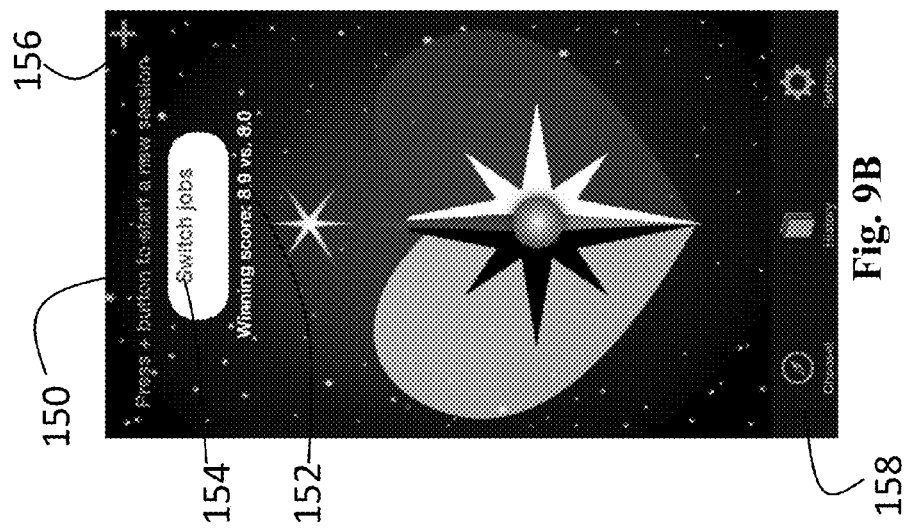
Figure 9A:
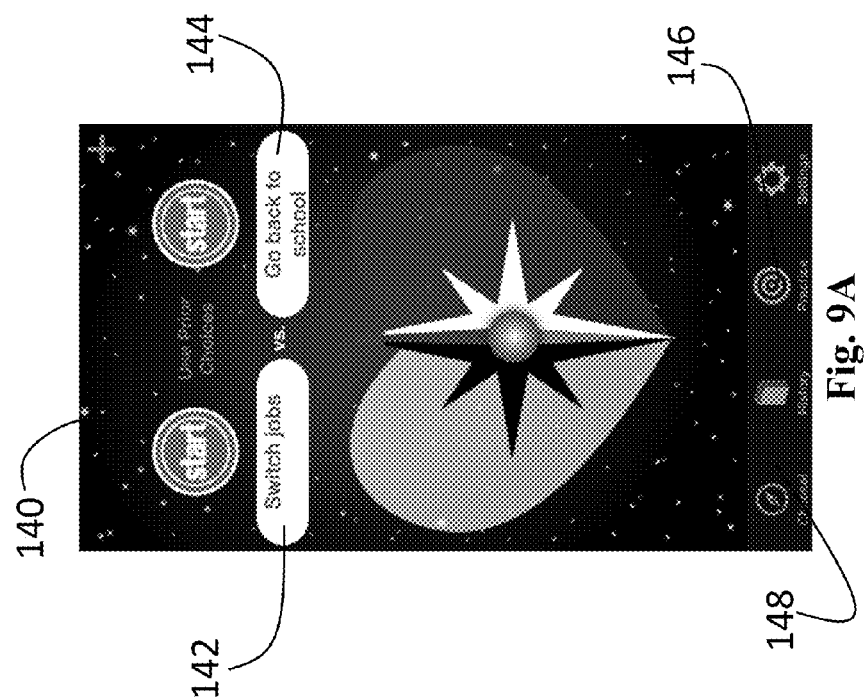

Several sample user interface screens are shown in FIGS. 9A-9F. Turning first to FIG. 9A, shown there is a select content screen 140. The select content screen 140 is used in the select content step 100 discussed in FIG. 5 in the embodiment depicted in FIG. 9A.

The screen consists of a first prompt 142 having a textual prompt and a user-selectable designation to begin the first prompt 142 (shown as a start button above the first prompt 142). A second prompt 144 likewise includes a corresponding user-selectable designation. While the prompts 142, 144 are depicted in left to right order, the analysis operates regardless of which is chosen first. The options bar 148 of the select content screen 140 includes a user selection option to invoke a practice mode 146, such as an active area of the screen 140. Otherwise the options bar 148 includes the functions to undertake a new analysis, to review history, and to review settings.

Further, the output screen 150 of the system per one embodiment is shown in FIG. 9B. The output screen 150 consists of an indication of the score associated with the prevailing stimulus 152, as well as an identifier of the prevailing stimulus 154. In one embodiment, the prevailing stimulus is the one with a higher score, in another embodiment, the stimulus with a specific frequency score is given the prevailing score. In the example embodiment shown in FIG. 9B, the prevailing score 152 is 8.9, while the prevailing stimulus 154 is the option for 'switching jobs.' In this embodiment, the user has the option of an additional iteration of the analysis by invoking the iterate option 156. The user can also review a history of analysis, begin a new session or review settings by invoking one of the options 158. While the system provides the user a score, it does not display to the user the underlying data, such as the inter-peak values, the frequency information, and the data bins used to assign scores.

Figure 9D:
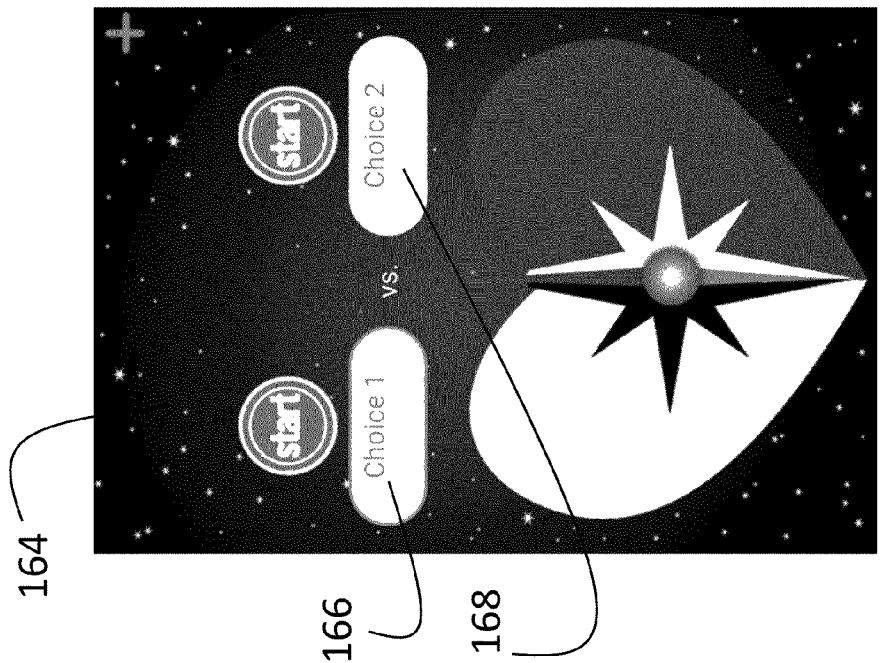
Figure 9C:
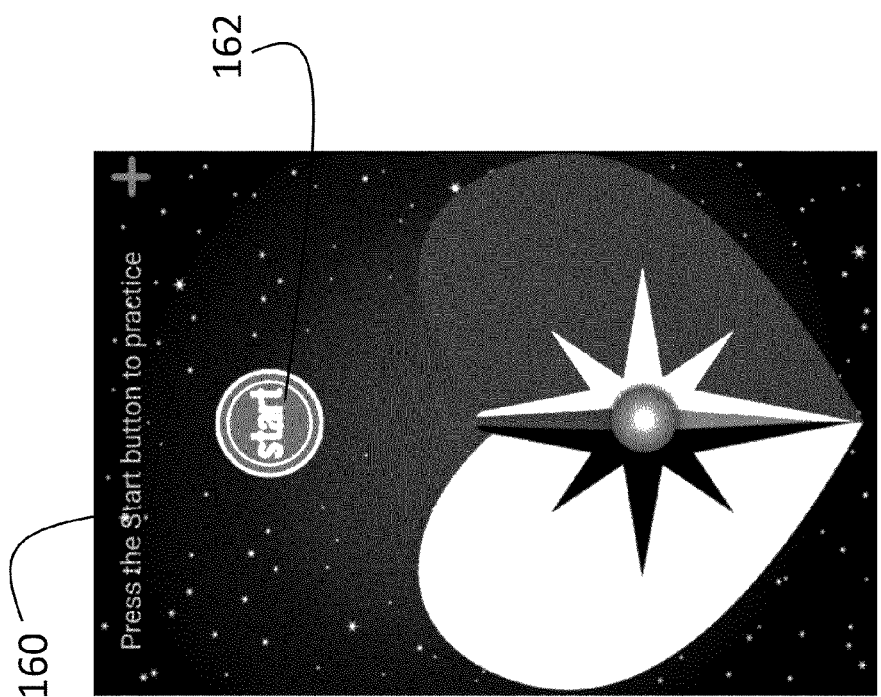

Turning to FIG. 9C, it depicts sample screen 160 showing the practice mode invoked by pressing the selection option 156, pursuant to one embodiment. The practice mode begins with a first screen 160 requiring the user to affirm the initiation of the practice mode by invoking the user option 162. FIG. 9D depicts sample screen 164 showing user options before choices are entered, with a first choice 166 and a second choice 168

One depiction of the screen used during the prompt user step 102 of an embodiment of the system is shown in a prompt screen 170 in FIG. 9E. The sample screen 170 consists of a reminder prompt 172 for the user to consider the effects of an associated option. In the embodiment shown in FIG. 9E, the prompt 172 consists of the instruction to "Focus on all outcomes of this choice." The screen 170 includes the actual subject matter of the analysis 174, such as the choice of "Go back to school" shown in FIG. 9E. Also included on the screen is a timer 176 indicating to the user the length of time that the subject matter of the analysis 174 will remain for analysis. The screen also includes an options bar 178.

An initialization screen 180, pursuant to one embodiment, displayed to the user upon the start of the analysis shown in FIG. 9F. The initialization screen consists of a user name selection area 182, a gender designation 184, and initial explanatory text 186. The initialization screen 180 further comprises one or more logos 188 to indicate to the user an analysis sponsoring entity.

Multiple Phase Operation

In one embodiment, the system operates in two phases: a data-gathering phase and an end-user phase. During the data-gathering phase the system is operated by one or more professionals who record physiological data from users in a controlled environment. The data outputs of this phase are used to designate the frequency bins of interest, and the correlations between psychophysiological responses and frequency responses.

In one embodiment, this testing phase comprises selecting a control group of users. The control group is presented with equivalent presentations, and responses to each presentation are recorded. A review of the frequency data is used to select determinant variables for each group of users. Once this data set is established, the questions are available for end-users.

The information displayed to the end users is designed to assist users in decision-making. It is not for improving the users emotional responses, or for the users to achieve higher emotional resiliency. Instead, the system is a decision-support system.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

The invention claimed is:

1. A data processing device controlling an image-recording device to capture a video comprising:
   determining whether said captured video which comprises a series of images depicts a test subject who is a user of the device, and
   extrapolating an emotional response of a detected test subject to choices displayed on a display device during a time period encompassed by said series of images;
   wherein the extrapolation of the emotional response measures the subject's time between heart rate peaks and wherein said captured video comprises a close-up depiction of a region of the subject's exposed skin, and wherein the time between heart rate peaks is converted to the frequency domain;
   wherein the extrapolation step assigns a previously tested mathematical index to data in the frequency domain to determine the emotional response of the user to each stimulus.

2. The data processing device of claim 1 wherein the determination step ensures that a users' finger is placed in close proximity to the image recording device.

3. The data processing device of claim 1 wherein said data processing device, display device, and image recording device comprise a multi-purpose phone having a camera and a touchscreen.

4. The data processing device of claim 1 wherein said extrapolation comprises detecting intervals between heart rate peaks using the captured video.

5. The data processing device of claim 4 wherein said captured video comprises red and green values of each frame of the captured video.

6. A data processing device controlling an image-recording device to capture a video comprising:
   determining whether said captured video which comprises a series of images, depicts a test subject who is a user of the device; and
   extrapolating the emotional response of a detected test subject to choices displayed on a display device during a time period encompassed by said series of images;
   wherein the extrapolation of the emotional response measures the subject's time between heart rate peaks and wherein said captured video comprises a close-up depiction of a region of the subject's exposed skin, and wherein the time between heart rate peaks is converted to the frequency domain;
   wherein the choices displayed on the display comprise a pair of binary choices shown to the user;
   wherein said user is provided with which of the binary choices has a stronger emotional response by the user.

7. The data processing device of claim 6 wherein all heart rate peaks are used in determining the intervals between heart rate peaks.

8. The data processing device of claim 1 wherein only some components of the captured video is used to determine the inter peak data which in turn is converted into the frequency domain to determine the emotional response of the user.

* * * * *